United States Patent
Sahabi et al.

(10) Patent No.: US 9,855,435 B2
(45) Date of Patent: Jan. 2, 2018

(54) SYSTEMS AND METHODS FOR LEADLESS PACEMAKER ELECTRONICS ASSEMBLIES

(71) Applicant: PACESETTER, INC., Sylmar, CA (US)

(72) Inventors: Kavous Sahabi, Winnetka, CA (US); Arees Garabed, North Hills, CA (US)

(73) Assignee: PACESETTER, INC., Sylmar, CA (US)

( * ) Notice: Subject to any disclaimer, the term of this patent is extended or adjusted under 35 U.S.C. 154(b) by 195 days.

(21) Appl. No.: 14/681,969

(22) Filed: Apr. 8, 2015

(65) Prior Publication Data
US 2016/0296760 A1    Oct. 13, 2016

(51) Int. Cl.
| A61N 1/00  | (2006.01) |
| A61N 1/375 | (2006.01) |
| A61N 1/362 | (2006.01) |
| A61N 1/05  | (2006.01) |

(52) U.S. Cl.
CPC ......... *A61N 1/3756* (2013.01); *A61N 1/0573* (2013.01); *A61N 1/362* (2013.01)

(58) Field of Classification Search
CPC ...... A61N 1/0573; A61N 1/362; A61N 1/057; A61N 1/375; A61N 1/3756; A61N 1/3752; A61N 1/3754; A61N 1/3758
See application file for complete search history.

(56) References Cited

U.S. PATENT DOCUMENTS

| 7,937,148 | B2 | 5/2011 | Jacobson |
| 7,945,333 | B2 | 5/2011 | Jacobson |
| 8,010,209 | B2 | 8/2011 | Jacobson |
| 8,352,025 | B2 | 1/2013 | Jacobson |
| 8,457,742 | B2 | 6/2013 | Jacobson |
| 2007/0088396 | A1 | 4/2007 | Jacobson |
| 2007/0088397 | A1 | 4/2007 | Jacobson |
| 2010/0305629 | A1* | 12/2010 | Lund ................... H01M 4/5835 607/2 |
| 2011/0190842 | A1* | 8/2011 | Johnson ................. A61N 1/375 607/37 |
| 2012/0151758 | A1* | 6/2012 | Primavera ............ A61N 1/3758 29/761 |
| 2013/0123875 | A1* | 5/2013 | Varady ................ A61N 1/3756 607/36 |

FOREIGN PATENT DOCUMENTS

| WO | 2007047681 A2 | 4/2007 |
| WO | 2007047681 A3 | 9/2008 |

* cited by examiner

*Primary Examiner* — Mallika D Fairchild

(57) ABSTRACT

The present disclosure provides leadless pacemaker systems and methods. A leadless pacemaker includes a battery subassembly, a feedthrough subassembly, and an electronics subassembly coupled between the battery subassembly and the feedthrough subassembly, the electronics subassembly including an electronics package, and a housing configured to provide a hermetic seal and comprising a first retaining feature and a second retaining feature configured to secure the electronics package within the housing.

12 Claims, 5 Drawing Sheets

SYSTEMS AND METHODS FOR LEADLESS PACEMAKER ELECTRONICS ASSEMBLIES

A. FIELD OF THE DISCLOSURE

The present disclosure relates generally to methods and systems for cardiac pacing, and more particularly, to electronics assemblies for leadless pacemakers.

B. BACKGROUND ART

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is typically performed by a pulse generator implanted subcutaneously or sub-muscularly in or near a patient's pectoral region. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, several well-known difficulties exist. For example, a pulse generator, when located subcutaneously, presents a bulge in the skin that patients can find unsightly or unpleasant. Although sub-muscular or abdominal placement can address some concerns, such placement involves a more difficult surgical procedure for implantation and adjustment, which can prolong patient recovery. Further, the lead body can be cut inadvertently during surgery by a tool, or cut after surgery by repeated stress on a ligature used to hold the lead body in position. Moreover, repeated movement for hundreds of millions of cardiac cycles can cause lead conductor breakage or insulation damage anywhere along the lead body.

Many of the issues associated with conventional pacemakers are resolved by the development of a self-contained and self-sustainable pacemaker, or so-called leadless pacemaker, as described herein.

BRIEF SUMMARY OF THE DISCLOSURE

In one embodiment, the present disclosure is directed to a leadless pacemaker. The leadless pacemaker includes a battery subassembly, a feedthrough subassembly, and an electronics subassembly coupled between the battery subassembly and the feedthrough subassembly, the electronics subassembly including an electronics package, and a housing configured to provide a hermetic seal and comprising a first retaining feature and a second retaining feature configured to secure the electronics package within the housing.

In another embodiment, the present disclosure is directed to an electronics subassembly for a leadless pacemaker. The electronics subassembly includes an electronics package, and a housing configured to provide a hermetic seal and comprising a first retaining feature and a second retaining feature configured to secure the electronics package within the housing.

In another embodiment, the present disclosure is directed to a method of assembling a leadless pacemaker. The method includes inserting an electronics package into a housing to form an electronics subassembly, wherein the housing provides a hermetic seal and includes a first retaining feature and a second retaining feature that engage the electronics package, coupling a first end of the electronics subassembly to a feedthrough subassembly, and coupling a second end of the electronics subassembly to a battery subassembly.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
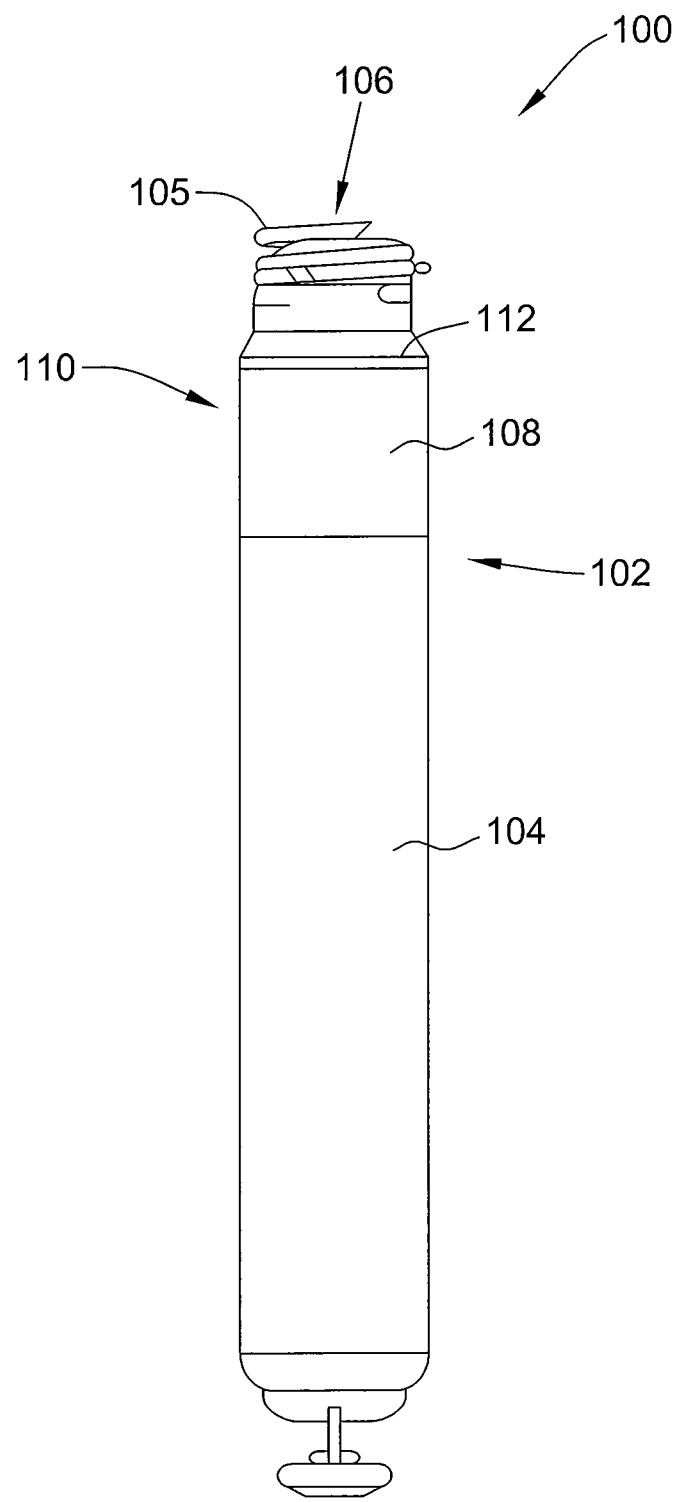
FIG. 1 is a schematic view of one embodiment of a leadless pacemaker.

The systems and methods described herein facilitate reducing the cost and complexity of manufacturing leadless pacemakers. A leadless pacemaker includes a battery subassembly, a feedthrough subassembly, and an electronics subassembly coupled between the battery subassembly and the feedthrough subassembly. The electronics subassembly includes an electronics package, and a housing configured to provide a hermetic seal and comprising a first retaining feature and a second retaining feature configured to secure the electronics package within the housing.

In some embodiments of a cardiac pacing system, cardiac pacing is provided without a pulse generator located in the pectoral region or abdomen, without an electrode-lead separate from the pulse generator, without a communication coil or antenna, and without an additional requirement on battery power for transmitted communication.

An embodiment of a cardiac pacing system configured to attain these characteristics includes a leadless cardiac pacemaker that is substantially enclosed in a hermetic housing suitable for placement on or attachment to the inside or outside of a cardiac chamber. The pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing may include contain a primary battery to provide power for pacing, sensing, and communication, for example bidirectional communication. The housing may optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Examples of such leadless biostimulators are described in the following publications, the disclosures of which are incorporated by reference:
(1) U.S. Pat. No. 8,457,742;
(2) U.S. Published Application No. 2007/0088396A1;
(3) U.S. Published Application 200710088397A1;
(4) U.S. Pat. No. 8,352,025;
(5) U.S. Pat. No. 7,937,148;
(6) U.S. Pat. No. 7,945,333;
(7) U.S. Pat. No. 8,010,209; and
(8) Intl Publication WO/2007/047681A2.

Self-contained or leadless pacemakers or other biostimulators are typically fixed to an intracardial implant site by using a screw or helical member that screws into the myocardium. In case of malfunction, it is highly desirable to be able to retrieve the leadless pacemaker of biostimulators both acutely (during the implantation procedure) or chronically, after a period of time post implantation minimally invasively.

Referring now to FIG. 1, a leadless cardiac pacemaker is indicated generally at 100. In this embodiment, leadless cardiac pacemaker includes a hermetic housing 102 with electrodes 104 and 106 disposed thereon. As shown, electrode 106 can be separated from but surrounded partially by a fixation mechanism 105, and the 104 can be disposed on the housing 102. Fixation mechanism 105 can be a fixation helix, a plurality of hooks, barbs, or other attaching features configured to attach the pacemaker to tissue, such as heart tissue.

Hermetic housing 102 can also include an electronics compartment 110 within the housing that contains the electronic components necessary for operation of the pacemaker, including, for example, a pulse generator, communication electronics, a battery, and a processor for operation. Hermetic housing 102 can be adapted to be implanted on or in a human heart, and can be cylindrically shaped, rectangular, spherical, or any other appropriate shapes, for example.

Hermetic housing 102 may be manufactured from a conductive, biocompatible, inert, and anodically safe material such as titanium, 316L stainless steel, or other similar materials. Hermetic housing 102 can further comprise an insulator disposed on the conductive material to separate electrodes 104 and 106. The insulator can be an insulative coating on a portion of the housing between the electrodes, and can comprise materials such as silicone, polyurethane, parylene, or another biocompatible electrical insulator commonly used for implantable medical devices. In this embodiment, a single insulator 108 is disposed along the portion of hermetic housing 102 between electrodes 104 and 106. In some embodiments, hermetic housing 102 itself may be an insulator instead of a conductor, such as an alumina ceramic or other similar materials, and electrodes 104 and 106 may be disposed upon hermetic housing 102.

As shown in FIG. 1, pacemaker 100 may include a header assembly 112 to isolate electrode 104 from electrode 106. Header assembly 112 may be made from PEEK, tecothane or another biocompatible plastic, and can contain a ceramic to metal feedthrough, a glass to metal feedthrough, or other any other appropriate feedthrough insulator as known in the art.

Figure 2:
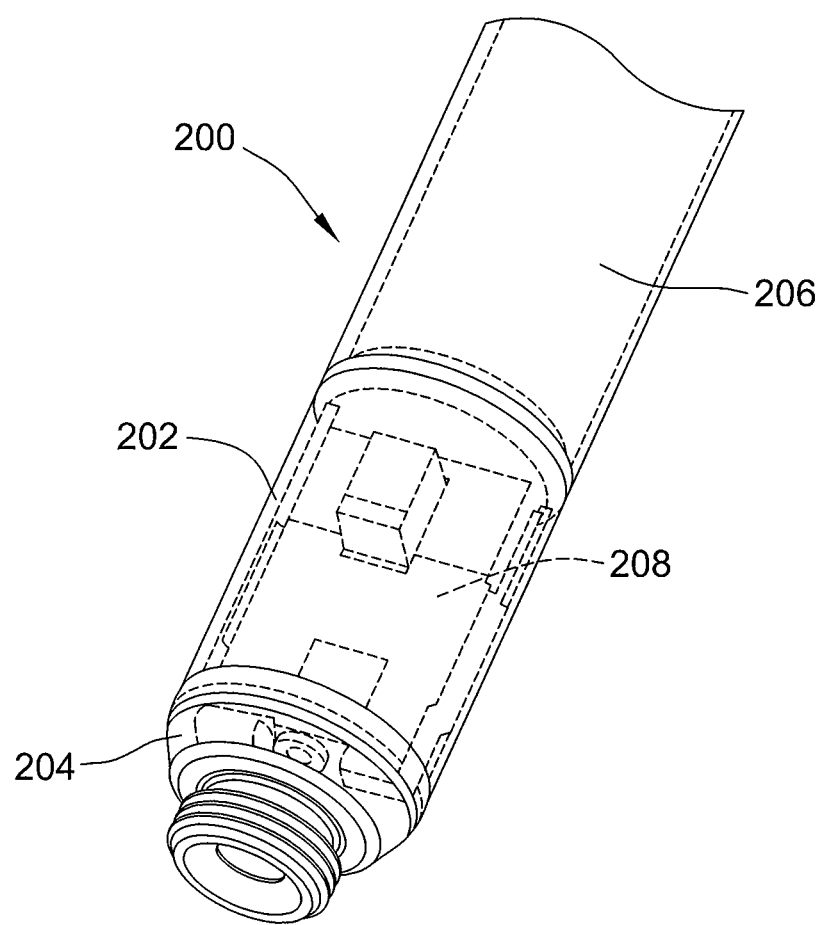
FIG. 2 is a perspective view of a portion of one embodiment of a leadless pacemaker.

FIG. 2 is a perspective view of a portion of a pacemaker 200, such as pacemaker 100. Pacemaker 200 includes an electronics subassembly 202, a feedthrough subassembly 204, and a battery subassembly 206. In this embodiment, electronics subassembly 202 is coupled between feedthrough subassembly 204 and battery subassembly 206. Electronics subassembly 202 houses an electronics package 208, as described herein.

Figure 3:
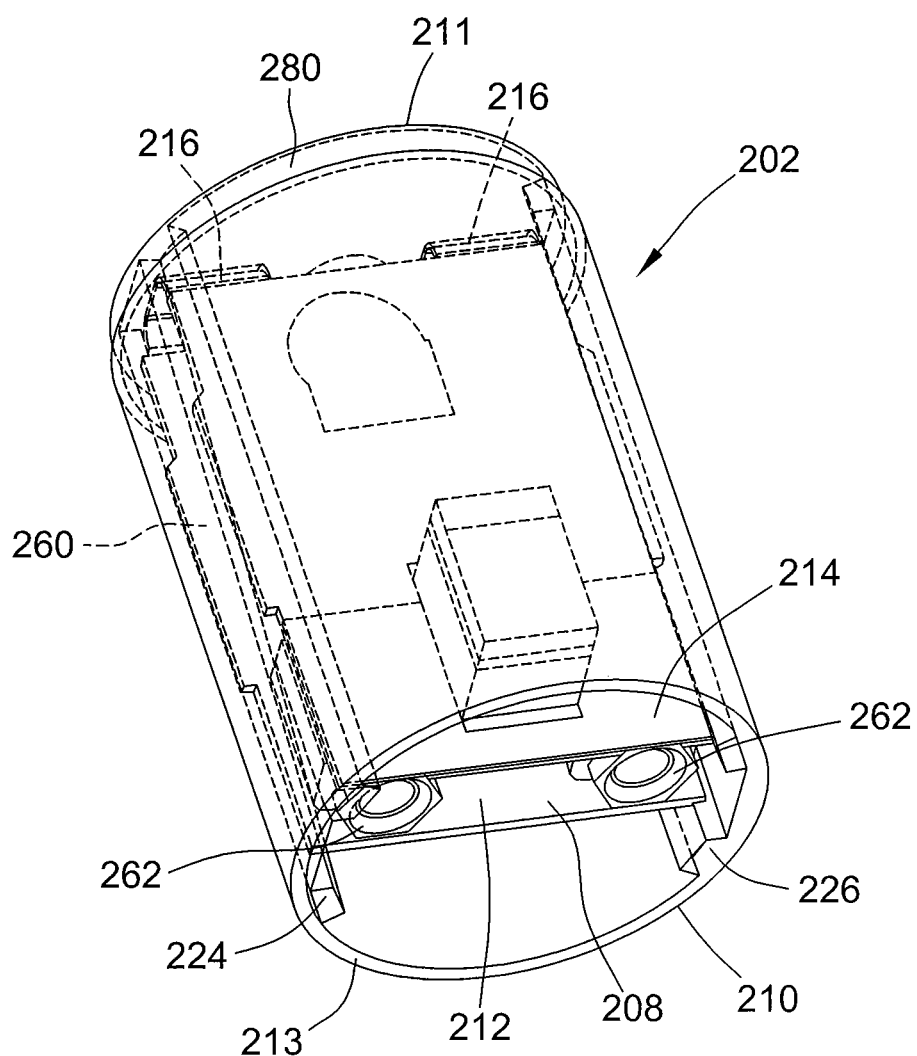
FIG. 3 is a perspective view of an electronics subassembly that may be used with the pacemaker shown in FIG. 2.
Figure 4:
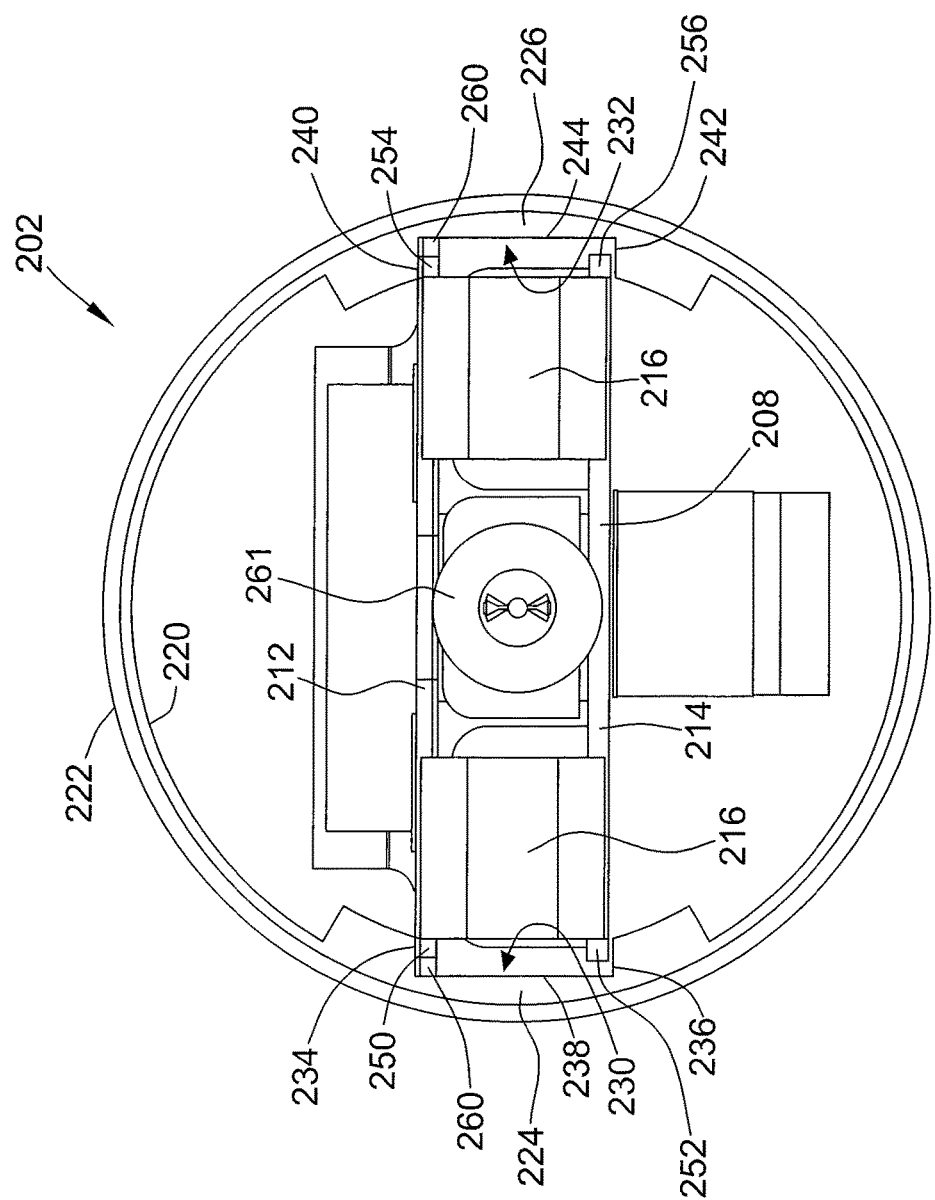
FIG. 4 is an end view of the electronics subassembly shown in FIG. 3.

FIG. 3 is a perspective view of electronics subassembly 202, and FIG. 4 is an end view of electronics subassembly 202. As shown in FIGS. 3 and 4, electronics subassembly 202 includes electronics package 208 positioned within a nose cone, or housing 210. Housing 210 extends from a first end 211 to a second end 213, and provides a hermetic seal for electronics package 208. Housing 210 couples to feedthrough subassembly 204 at first end 211, and couples to battery subassembly 206 at second end 213.

In this embodiment, electronics package 208 includes a plurality of components coupled to a first circuit board 212 and a second circuit board 214. First circuit board 212 and second circuit board 214 are connected to each other through a pair of flexible bands 216. As shown in FIGS. 3 and 4, flexible bands 216 enable first and second circuit boards 212 and 214 to be folded over one another. Further, flexible bands 216 have at least some resilience such that when first and second circuit boards 212 and 214 are folded over one another, first and second circuit boards 212 and 214 are biased to unfold from one another. This facilitates securing electronics package 208 in housing 210, as described herein.

As shown in FIG. 4, housing 210 is substantially annular and includes a radially inner surface 220 and a radially outer surface 222. A first retaining feature 224 and a second retaining feature 226 extend radially inward from radially inner surface 220. First and second retaining features 224 are located diametrically opposite one another, and facilitate retaining electronics package 208 in housing 210, as described herein.

First retaining feature 224 defines a first groove 230, and second retaining feature 226 defines a second groove 232. Specifically, first groove 230 is defined by a first upper wall 234, a first lower wall 236, and a first side wall 238 extending between first upper wall 234 and first lower wall 236. Similarly, second groove 232 is defined by a second upper wall 240, a second lower wall 242, and a second side wall 244 extending between second upper wall 240 and second lower wall 242. In this embodiment, first and second grooves 230 and 232 extend along an entire length of housing 210 (i.e., from first end 211 to second end 213). Alternatively, first and second grooves 230 and 232 may only extend along a portion of the length of housing 210.

To position electronics package 208 in housing 210 first and second circuit boards 212 and 214 are folded over one another and inserted into housing 210. Specifically, first and second circuit boards 212 and 214 are inserted into housing 210 such that a first edge 250 of first circuit board 212 and a first edge 252 of second circuit board 214 are received within first groove 230, and such that a second edge 254 of first circuit board 212 and a second edge 256 of second circuit board 214 are received within second groove 232.

Once electronics package 208 is positioned within housing 210, first and second circuit boards 212 and 214, due to the biasing force provided by flexible bands 216, attempt to unfold relative to one another. Accordingly, first circuit board first edge 250 is biased against first upper wall 234, first circuit board second edge 254 is biased against second upper wall 240, second circuit board first edge 252 is biased against first lower wall 236, and second circuit board second edge 256 is biased against second lower wall 242. The biasing of first and second circuit boards 212 and 214 against upper and lower walls 234, 240, 236, and 242 facilitates securing electronics package 208 within housing 210. In this embodiment, first circuit board first edge 250 and first circuit board second edge 254 each include an offset portion 260. Offset portions 260 contact first and second side walls 238 and 244.

As shown in FIG. 4, in this embodiment, electronics package 208 includes a feedthrough connector 261 (e.g., a spring connector) for connecting feedthrough subassembly 204 to electronics subassembly 202. Further, electronics package 208 includes a pair of battery connectors 262 (e.g., spring connectors) for connecting battery subassembly 206 to electronics subassembly 202.

Figure 5:
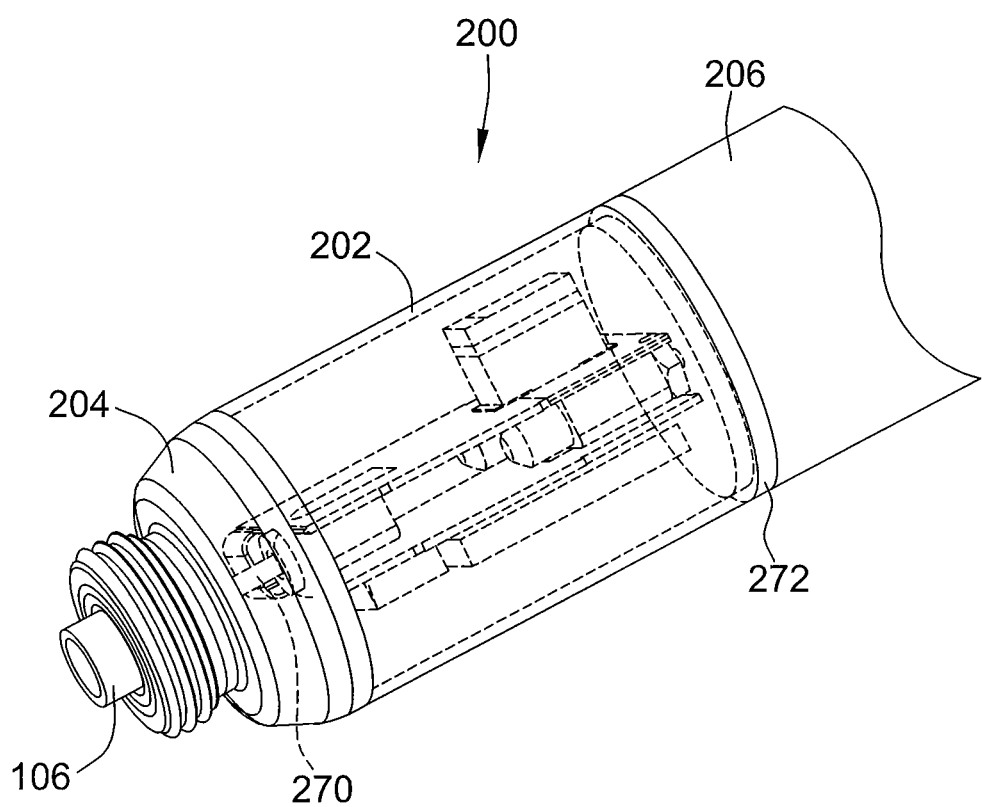
FIG. 5 is a perspective view of a portion of the leadless pacemaker shown in FIG. 2.

FIG. 5 is a perspective view of a portion of pacemaker 200. As shown in FIG. 5, a wire 270 extends from feedthrough connector 261 to an electrode 106 to facilitate coupling electronics subassembly 202 to feedthrough subassembly 204. Further, in this embodiment, electronics subassembly 202 is coupled to battery subassembly 206 using battery connectors 262 and a coupling ring 272. Using connectors 261 and 262 for the coupling between electronics subassembly 202 and feedthrough and battery subassemblies 204 and 206 facilitates simplifying the manufacturing and reducing the cost of pacemaker 200.

Alternatively, electronics subassembly 202 may be coupled to feedthrough subassembly 204 and battery subassembly 206 using any suitable techniques. For example, in some embodiments, electronics subassembly 202 is coupled to feedthrough subassembly 204 via welding (e.g., laser welding). To prevent damage to electronics package 208 from welding, in at least some embodiments, housing 210 includes a protective band 280, shown best in FIG. 3. Protective band 280 is a machined annular component positioned at first end 211 of housing 210. In this embodiment, protective band 280 is integrally formed as part of housing 210. Alternatively, protective band 280 may be a separate component coupled to housing 210.

At least some known leadless pacemakers include a metallic frame positioned within a housing, or nose cone. The metallic frame facilitates securing electronics within the housing and protecting the electronics from welding damage. In contrast, the systems and methods described herein provide a housing having retaining features formed thereon for securing an electronics package. Accordingly, the systems and methods described herein eliminate the need for a separate, metallic frame, simplifying the manufacturing and reducing the cost of a leadless pacemaker. Further, in at least some embodiments, the leadless pacemaker described herein includes connectors that eliminate the need to weld components together.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A leadless pacemaker comprising:
    a battery subassembly;
    a feedthrough subassembly; and
    an electronics subassembly coupled between the battery subassembly and the feedthrough subassembly, the electronics subassembly comprising:
    an electronics package; and
    a housing configured to provide a hermetic seal and having a first retaining feature and a second retaining feature configured to secure the electronics package within the housing;
    wherein the housing is an annular housing comprising a wall with a radially inner surface and a radially outer surface;
    wherein the first and second retaining features extend radially inward from the radially inner surface;
    wherein the first and second retaining features are located diametrically opposite one another in a radial direction; and
    wherein each of the first and second retaining features comprises:
        an upper wall adjacent to the radially inner surface;
        a lower wall adjacent to the radially inner surface; and
        a side wall extending between the upper and lower walls, wherein the upper wall, the lower wall, and the side wall define a groove configured to receive the electronics package, wherein the groove extends longitudinally with the housing.

2. The leadless pacemaker of claim 1, wherein the electronics package comprises a first circuit board foldably coupled to a second circuit board.

3. The leadless pacemaker of claim 1, wherein the electronics package comprises a feedthrough connector that facilitates coupling the electronics subassembly to the feedthrough subassembly.

4. The leadless pacemaker of claim 1, wherein the electronics package comprises a pair of battery connectors that facilitate coupling the electronics subassembly to the battery subassembly.

5. An electronics subassembly for a leadless pacemaker, the electronics subassembly comprising:
- an electronics package; and
- a housing configured to provide a hermetic seal and having a first retaining feature and a second retaining feature configured to secure the electronics package within the housing;
- wherein the housing is an annular housing comprising a wall with a radially inner surface and a radially outer surface;
- wherein the first and second retaining features extend radially inward from the radially inner surface;
- wherein the first and second retaining features are located diametrically opposite one another in a radial direction; and
- wherein each of the first and second retaining features comprises:
  - an upper wall adjacent to the radially inner surface;
  - a lower wall adjacent to the radially Inner surface; and
  - a side wall extending between the upper and lower walls, wherein the upper wall, the lower wall, and the side wall define a groove configured to receive the electronics package, wherein the groove extends longitudinally with the housing.

6. The electronics subassembly of claim 5, wherein the electronics package comprises a first circuit board foldably coupled to a second circuit board.

7. The electronics subassembly of claim 5, wherein the electronics package comprises a feedthrough connector that facilitates coupling the electronics subassembly to a feedthrough subassembly.

8. The electronics subassembly of claim 5, wherein the electronics package comprises a pair of battery connectors that facilitate coupling the electronics subassembly to a battery subassembly.

9. A method of assembling a leadless pacemaker, the method comprising:
- inserting an electronics package into a housing to form an electronics subassembly, wherein the housing provides a hermetic seal and has a first retaining feature and a second retaining feature that engage the electronics package;
- coupling a first end of the electronics subassembly to a feedthrough subassembly; and
- coupling a second end of the electronics subassembly to a battery subassembly;
- wherein inserting an electronics package into a housing comprises inserting the electronics package into an annular housing having a wall with a radially inner surface and a radially outer surface, the first and second retaining features extending radially inward from the radially inner surface; and
- wherein inserting an electronics package into a housing comprises inserting the electronics package into a housing in which each of the first and second retaining features include an upper wall adjacent to the radially inner surface, a lower wall adjacent to the radially inner surface, and a side wall extending between the upper and lower walls, the upper wall, the lower wall, and the side wall defining a groove that receives the electronics package, wherein the groove extends longitudinally with the housing.

10. The method of claim 9, wherein inserting an electronics package into a housing comprises inserting an electronics package including a first circuit board foldably coupled to a second circuit board.

11. The method of claim 9, wherein coupling a first end of the electronics subassembly to a feedthrough subassembly comprises coupling the first end of the electronics subassembly to the feedthrough subassembly using a feedthrough connector included on the electronics package.

12. The method of claim 9, wherein coupling a second end of the electronics subassembly to a battery subassembly comprises coupling the second end of the electronics subassembly to the battery subassembly using a pair of battery connectors included on the electronics package.

* * * * *